(12) United States Patent
Mashiach et al.

(10) Patent No.: US 8,585,617 B2
(45) Date of Patent: Nov. 19, 2013

(54) DIAGNOSIS AND PREDICTION OF OBSTRUCTIVE SLEEP APNEA

(75) Inventors: Adi Mashiach, Tel Aviv (IL); Yossef Mashiach, Ra'anana (IL)

(73) Assignee: Nyxoah SA, Mont-St-Guibert (BE)

( * ) Notice: Subject to any disclaimer, the term of this patent is extended or adjusted under 35 U.S.C. 154(b) by 711 days.

(21) Appl. No.: 12/642,866

(22) Filed: Dec. 21, 2009

(65) Prior Publication Data

US 2011/0152965 A1    Jun. 23, 2011

(51) Int. Cl.
*A61B 5/103* (2006.01)
*A61B 5/08* (2006.01)

(52) U.S. Cl.
USPC .......................................... 600/595; 600/534

(58) Field of Classification Search
USPC ................................................. 600/595, 534
See application file for complete search history.

(56) References Cited

U.S. PATENT DOCUMENTS

| | | | |
|---|---|---|---|
| 4,765,983 A * | 8/1988 | Takayanagi et al. ........... 424/434 |
| 5,485,851 A | 1/1996 | Erickson |
| 5,895,360 A * | 4/1999 | Christopherson et al. .... 600/529 |
| 6,572,543 B1 | 6/2003 | Christopherson et al. |
| 7,374,540 B2 | 5/2008 | Schnall |
| 2004/0172089 A1 | 9/2004 | Whitehurst et al. |
| 2005/0010265 A1 | 1/2005 | Baru Fassio et al. |
| 2006/0114104 A1 * | 6/2006 | Scaramozzino ............. 340/10.2 |
| 2006/0180647 A1 * | 8/2006 | Hansen ......................... 235/375 |
| 2007/0222560 A1 * | 9/2007 | Posamentier ............... 340/10.2 |
| 2008/0030363 A1 * | 2/2008 | Rezvani et al. .......... 340/825.22 |
| 2008/0103407 A1 | 5/2008 | Bolea et al. |
| 2008/0109046 A1 * | 5/2008 | Lima et al. ...................... 607/42 |
| 2008/0165058 A1 * | 7/2008 | Ayachitula et al. ........... 342/359 |
| 2009/0048647 A1 * | 2/2009 | Tingey ............................ 607/62 |
| 2009/0069648 A1 * | 3/2009 | Irazoqui et al. ............... 600/302 |
| 2009/0078274 A1 | 3/2009 | Bhat et al. |
| 2010/0114190 A1 | 5/2010 | Bendett et al. |
| 2010/0191136 A1 | 7/2010 | Wolford |
| 2010/0292527 A1 | 11/2010 | Schneider et al. |
| 2011/0065979 A1 | 3/2011 | Lehrman et al. |
| 2011/0071591 A1 | 3/2011 | Bolea et al. |

FOREIGN PATENT DOCUMENTS

| | | |
|---|---|---|
| WO | WO 2007/098202 | 8/2007 |
| WO | WO 2011/077433 | 6/2011 |

* cited by examiner

*Primary Examiner* — Patricia Mallari
*Assistant Examiner* — Yunqing Wang
(74) *Attorney, Agent, or Firm* — Finnegan, Henderson, Farabow Garrett & Dunner LLP

(57) ABSTRACT

A tongue location monitoring system, including, one or more position circuits that respond to transmissions from a transceiver, a transceiver that transmits to the one or more position circuits, a control circuit coupled to the transceiver: wherein the control circuit determines the location of a person's tongue based on the responses of the position circuits; and wherein either the transceiver or the position circuits are implanted in the muscle of the person's tongue or placed on the tongue, and the latter is placed outside the person's head.

16 Claims, 3 Drawing Sheets

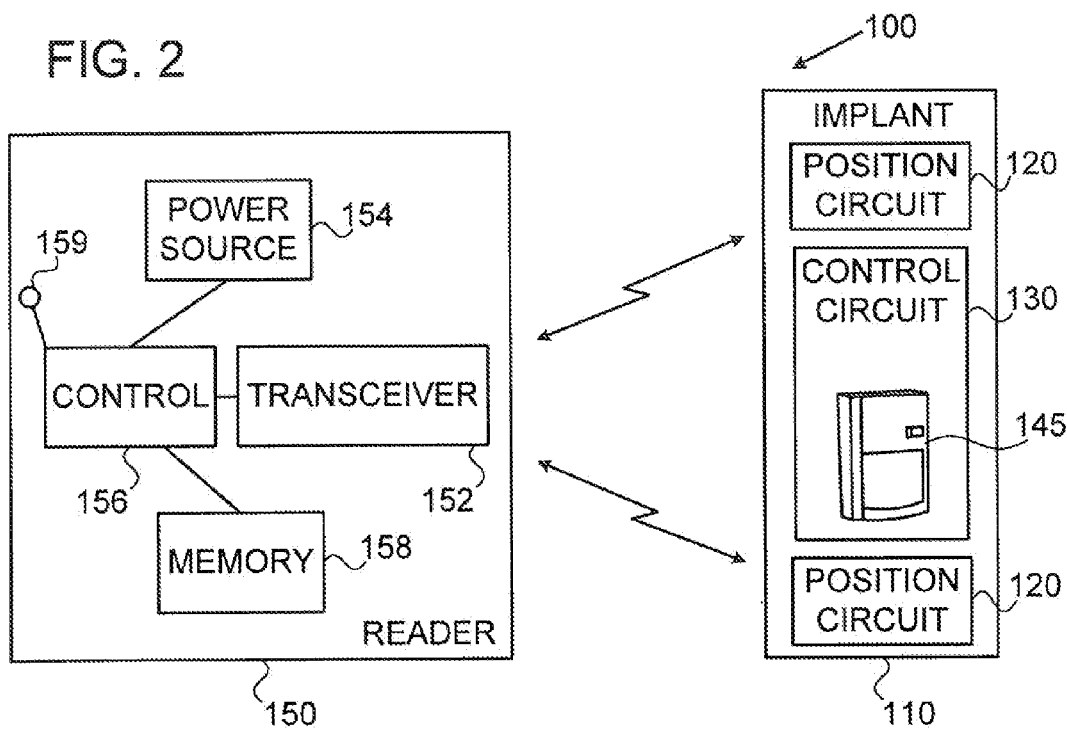
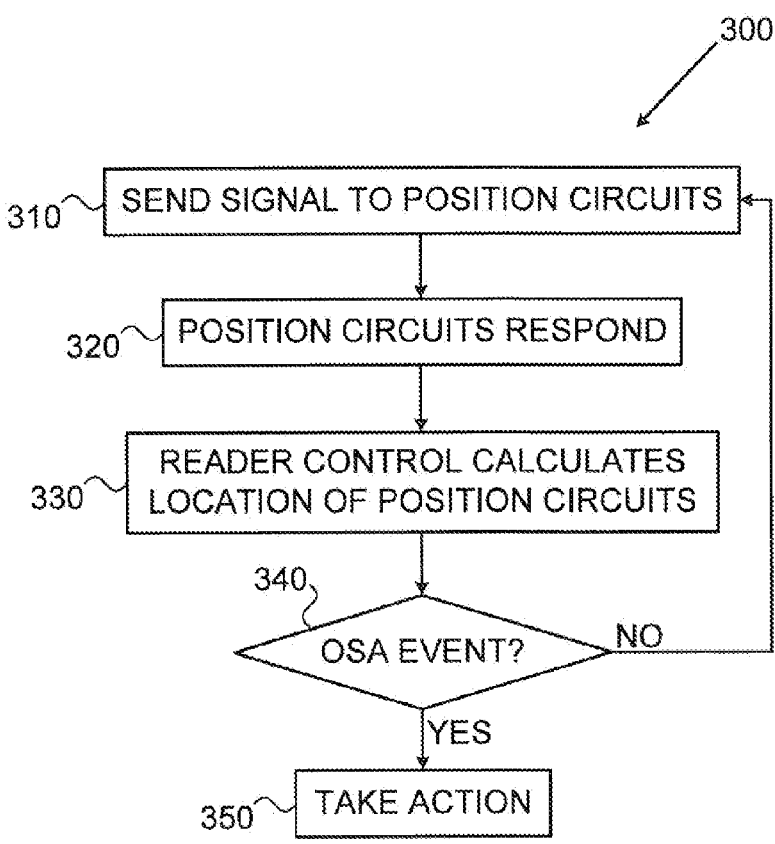

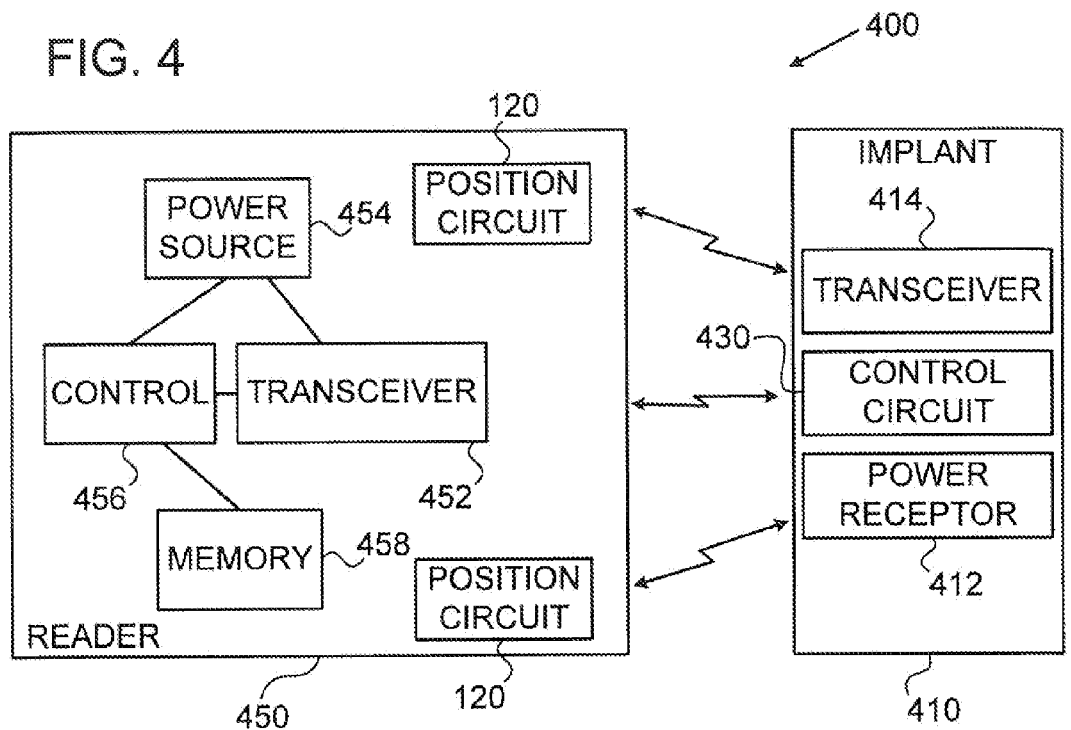
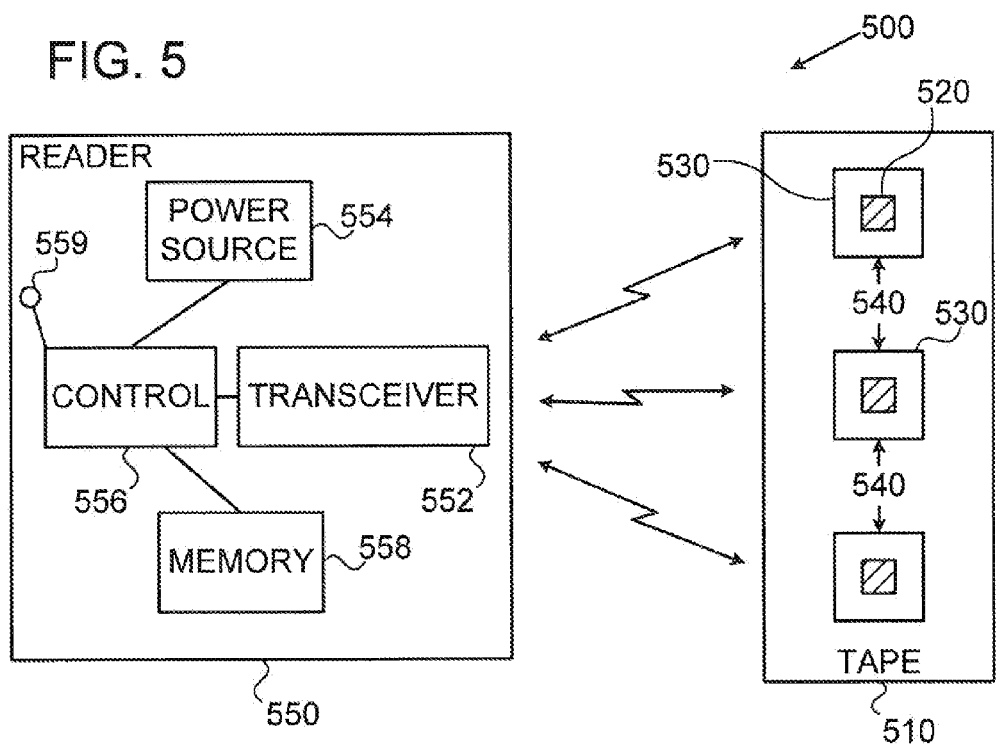

DIAGNOSIS AND PREDICTION OF OBSTRUCTIVE SLEEP APNEA

FIELD OF THE INVENTION

The present invention relates generally to a system and method of diagnosing and predicting obstructive sleep apnea based on the position of the tongue muscle.

BACKGROUND OF THE INVENTION

Typically obstructive sleep apnea (OSA) is diagnosed in a sleep laboratory by attaching the patient to various measurement devices, which measure parameters such as an Electroencephalography (EEG), an Electromyography (EMG) of respiratory muscles, a device for measuring blood Oxygen saturation and devices for measuring other parameters while the patient sleeps.

Obstructive sleep apnea is the most common type of sleep apnea. One of its causes is the collapse of the tongue muscle, wherein the collapsed tongue muscle obstructs the airway and causes an OSA event.

Various devices have been designed to enable diagnosing the occurrence of OSA without going to a sleep laboratory. One example is a device that monitors changes in the peripheral arterial tone as manifested by changes in the pulsatile arterial blood volume in a terminal extremity of a body part, e.g. a digit (finger or toe) of the subject, as described in U.S. Pat. No. 7,374,540.

Other methods of diagnosing OSA include implantable systems, for example a system that uses an intra-thoracic pressure sensor that senses breathing movements for treating respiratory disorders as described in U.S. Pat. No. 6,572,543. In US patent application publication no. US 2008/0103407 a system that senses breathing movements by applying an implantable bio-impedance sensor is described. In US patent application publication no. US 2009/0078274 an electro active polymer metal composite sensor is attached to a region in an airway passage of an oral cavity. The electrical output may be wirelessly transmitted to signify an obstructive sleep apnea event.

Other methods include a contact microphone that detects sounds and/or vibrations, and yet other methods include temperature sensors that detect temperature changes when an obstructive sleep apnea event occurs that result from the event.

Upon detection of the occurrence of the OSA event various remedial measures can be taken, for example activating an implanted stimulator or an external device.

SUMMARY OF THE INVENTION

An aspect of an embodiment of the invention, relates to a system and method for diagnosing and predicting an OSA event by monitoring the location of the tongue muscle. In an exemplary embodiment of the invention, a reader is placed outside a patient's head and one or more position circuits are placed on the patient's tongue or implanted in the tongue. Optionally, the reader transmits signals to the position circuits and receives a signal back from the position circuits. The returned signal is used to determine the location of the position circuits relative to the reader. Optionally, the reader repeatedly queries the position circuits, so that it can monitor the motion of the tongue muscle.

In some embodiments of the invention, the position circuits are passive RFID tags. Alternatively, the position circuits may be active RFID tags, BT transceivers, WiFi transceivers or any other type of wireless transmitters/receivers. In an exemplary embodiment of the invention, the position circuits are implanted directly into the tongue muscle. Alternatively, the position circuits are embedded in an implantable encasement that provides other functions such as to stimulate the tongue muscle.

In some embodiments of the invention, the position circuits are embedded in an adhesive biodegradable tape that can be placed on the patient's tongue before going to sleep. Optionally, while the patient is sleeping the position circuits will accept transmissions from the external reader and reply to the transmissions. In an exemplary embodiment of the invention, after a predetermined time the tape will degrade and the position circuits will exit through the digestive system.

In some embodiments of the invention, the position circuits are placed in the external reader. Optionally, the reader wirelessly transmits power to an implant in the patient's tongue and the implant transmits a signal to the position circuits.

In some embodiments of the invention, the reader determines the location of the position circuits and optionally monitors the motion of the position circuits. Optionally, the reader stores the information in a non-volatile memory for analysis at a later date, for example by a practitioner on a computer to diagnose the patient. Alternatively or additionally, the reader may transmit instructions to an implant or to other devices to act upon the information, for example to stimulate the tongue muscle when sensing that an OSA event is about to occur and prevent it from occurring.

There is thus provided according to an exemplary embodiment of the invention, a tongue location monitoring system, comprising:

one or more position circuits that respond to transmissions from a transceiver;

a transceiver that transmits to the one or more position circuits;

a control circuit coupled to the transceiver;

wherein the control circuit determines the location of a person's tongue based on the responses of the position circuits; and wherein either the transceiver or the position circuits are implanted in the person's tongue or placed on the tongue, and the latter is placed outside the person's head.

In an exemplary embodiment of the invention, the position circuits are implanted in the tongue muscle. Optionally, the transceiver is implanted in the tongue muscle. In an exemplary embodiment of the invention, the position circuits are embedded in an implantable stimulator that is implanted in the tongue muscle and the implantable stimulator is adapted to stimulate the tongue muscle. Optionally, the position circuits are embedded in a biodegradable tape that is adhesively attached to the tongue. In an exemplary embodiment of the invention, the control circuit determines the location of the tongue based on the travel time of the signal to the position circuit and back. Optionally, the control circuit determines the location of the tongue based on the strength of the signal returning to the transceiver. In an exemplary embodiment of the invention, an obstructive sleep apnea event is detected by monitoring the location of the tongue. Optionally, an obstructive sleep apnea event is detected by monitoring the angle of arrival of a response signal from the position circuits. In an exemplary embodiment of the invention, the position circuits are queried sequentially. Alternatively, the position circuits are queried in parallel. Further alternatively, the position circuits are queried continuously. Further alternatively, the position circuits are queried periodically. In an exemplary embodiment of the invention, the transceiver is provided power wirelessly and the transceiver queries the position circuits as long as it is provided power wirelessly.

There is further provided according to an exemplary embodiment of the invention, a method of monitoring the location of the tongue, comprising:

positioning either a transceiver or one or more position circuits as implants in a person's tongue or on the tongue, and positioning the latter outside the person's head;

transmitting signals from the transceiver to the position circuits;

receiving a response from the position circuits;

calculating the location of the position circuits relative to the transceiver from the response;

determining if an obstructive sleep apnea event is about to occur based on the calculated locations.

In an exemplary embodiment of the invention, the position circuits are implanted in the tongue or on the tongue. Alternatively, the position circuits are positioned outside the head. In an exemplary embodiment of the invention, the muscle of the tongue is stimulated responsive to the determining.

BRIEF DESCRIPTION OF THE DRAWINGS

The present invention will be understood and better appreciated from the following detailed description taken in conjunction with the drawings. Identical structures, elements or parts, which appear in more than one figure, are generally labeled with the same or similar number in all the figures in which they appear, wherein;

FIG. 2 is a schematic block diagram of a tongue location monitoring system with a reader and an implant with position circuits embedded therein, according to an exemplary embodiment of the invention;

FIG. 3 is a flow diagram of the process of monitoring the position of position circuits, according to an exemplary embodiment of the invention;

FIG. 4 is a schematic block diagram of an alternative tongue location monitoring system with a reader and implant, according to an exemplary embodiment of the invention; and FIG. 5 is a schematic block diagram of a tongue location monitoring system with a reader and a biodegradable tape with position circuits embedded therein, according to an exemplary embodiment of the invention.

DETAILED DESCRIPTION

Figure 1:
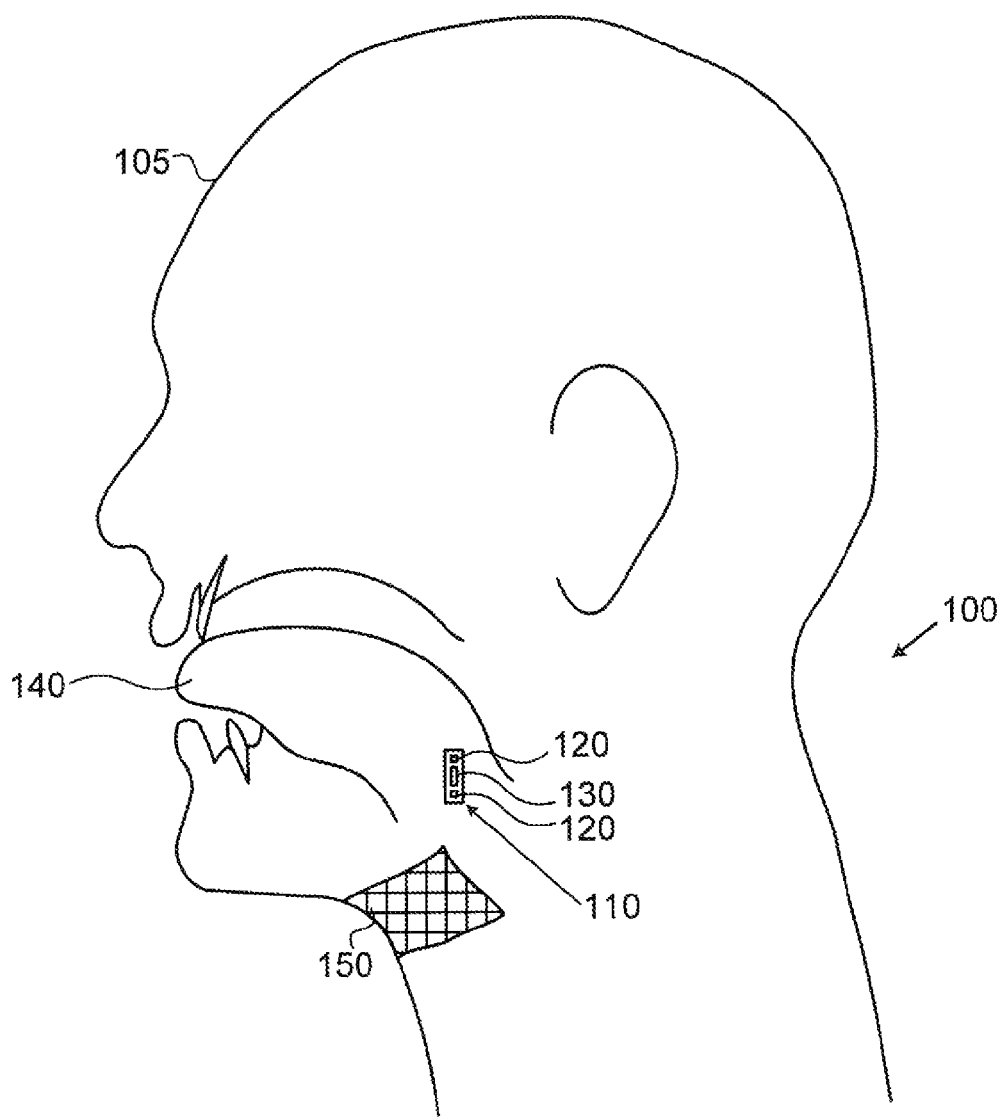
FIG. 1 is a schematic illustration of a patient's head with a tongue location monitoring system, according to an exemplary embodiment of the invention.

The present disclosure incorporates by reference U.S. patent application Ser. No. 12/581,907 filed Oct. 20, 2009 by the instant inventor, the disclosure of which is incorporated herein by reference describing a small implantable stimulator for dealing with an OSA event.

FIG. 1 is a schematic illustration of a patient's head 105 with a tongue location monitoring system 100, according to an exemplary embodiment of the invention. In an exemplary embodiment of the invention, system 100 includes an implant 110 implanted in the muscle of a patient's tongue 140, and an external reader 150 (for a non-limiting example, an adhesive patch that is attached to the patient's check or neck). Optionally, the implant 110 includes one or more position circuits 120 that enable reader 150 to locate the distance and/or angle and/or position to the position circuits 120 and monitor their relative position. In some embodiments of the invention, position circuits 120 may be radio frequency identification tags (RFID tags) placed in implant 110. Alternatively, position circuits 120 may be implanted independently in one or more locations in the muscle of the patient's tongue. Optionally, the distance between the position circuits 120 may be a preselected value enforced by the encasement of implant 110 or may be a random value. The position circuits 120 can comprise one or more circuits. The position circuits 120 can be passive or active. Passive position circuits 120 may comprise RFID tags, induction tags and the like. Passive position circuits 120 may comprise devices which emit energy in response to the presence of predetermined energy. Active position circuits 120 may comprise a Bluetooth device, a WiFi device, a powered RFID tag and the like. Active position circuits 120 may comprise devices which transmit a signal capable of being received by a receiver, such as reader 150.

In some embodiments of the invention, position circuits 120 may be passive circuits with or without an internal power source that respond to an external signal without requiring an internal power source. Alternatively, position circuits 120 may be active transmitters using an internal power source to function, for example an active RFID tag, a Bluetooth transmitter, a WiFi transmitter, or other types of transmitters.

In an exemplary embodiment of the invention, reader 150 is positioned outside of the user's head 105, for example in the form of a patch that can be adhesively attached to the patient's neck, cheek or below the patient's jaw, or to the vicinity thereof. Optionally, reader 150 may be in the form of a necklace or a necktie or other wearable items to make it less conspicuous.

FIG. 2 is a schematic block diagram of tongue location monitoring system 100 including reader 150 and implant 110 with position circuits 120 embedded therein, according to an exemplary embodiment of the invention. Optionally, reader 150 is adapted to transmit and/or receive signals from position circuits 120 and determine from the transmissions a relative position of the tongue muscle. In some embodiments of the invention, the position is determined based on the travel time of the signal to position circuits 120 and from position circuits 120 to reader 150. Alternatively, other methods known in the art are used to determine the location of position circuits 120 relative to reader 150 as described below.

In an exemplary embodiment of the invention, reader 150 includes a transceiver 152 that transmits and/or receives signals to/from position circuits 120. In some embodiments of the invention, position circuits 120 are RFID tags, which respond to a specific signal. Optionally, position circuits 120 are relatively small so that they can easily be implanted in the tongue muscle, for example some RFID circuits are smaller than 0.05 mm×0.05 mm. In some embodiments of the invention, position circuits 120 are placed inside implant 110, which provides additional functions, for example stimulating the tongue muscle responsive to internal or external instructions. Optionally, implant 110 includes a control circuit 130 to provide the additional functions (e.g. stimulation, or communications with other external devices). In some embodiments of the invention, determination of the location of the position circuits 120 can be used to more accurately determine the location of implant 110, for example based on the location of multiple position circuits 120.

In an exemplary embodiment of the invention, reader 150 includes a power source 154 (e.g. a battery) and an activation switch 159. Optionally, reader 150 also includes a control circuit 156 and a memory 158 to control reader 150. Optionally, control circuit 156 includes a processor and is programmed to instruct transceiver 152 to transmit a specific signal for each position circuits 120, receive a response to the transmitted signal and calculate the distance based on the transmission.

In some embodiments of the invention, reader 150 includes a motion sensor 145. Motion sensor 145 is preferably coupled to control circuit 130. Motion sensor 145 can be an accelerometer, gyroscope, or any other device capable of indicating the implant 110 has changed its position, and optionally the directional vector of such change.

In some embodiments of the invention, calculation of the distance is based on the signal strength. Alternatively or additionally, the calculation is based on the travel time of the signal to position circuits 120 or the time for the round trip of the signal to position circuits 120 and back to reader 150. Optionally, when reader 150 is initially activated it is calibrated relative to position circuits 120 assuming that the tongue muscle is in a normal state. Optionally, the use of multiple position circuits 120 positioned at pre-selected locations relative to each other allows more accurate three-dimensional determination of the location of position circuits 120 relative to reader 150.

In an exemplary embodiment of the invention, an increase in distance beyond a threshold value in pre-determined directions will be an indication of an OSA event. In other exemplary embodiment of the invention, a decrease in distance beyond a threshold value in pre-determined directions will be an indication of an OSA event.

In some embodiments of the invention, the angle of arrival may be used to determine an OSA event. Optionally, reader 150 is calibrated upon activation to an initial angle between the reader and the position circuits 120. Optionally, a change in the angle of arrival of the signal that indicates movement of the tongue muscle toward the patient's back beyond a threshold value will indicate an OSA event.

In some other embodiments of the invention, the time of arrival (TOA) of the signal from the position circuits 120 to the reader 150 may indicate an OSA event. In some embodiments of the invention, the signal strength received by the reader 150 may indicate an OSA event. In some other embodiments of the invention, the signal strength correlated with TOA or time of travel, between the position circuit 120 and the reader 150, received by the reader 150 may indicate an OSA event. In some embodiments of the invention, the first detected signal received by the reader 150 after the activation of the position circuits 120 may indicate an OSA event.

In the previous examples, each indication noted as an indication of an OSA event may also be considered as a precursor or the onset of an OSA event. Thus, the present indications may provide an indication that an OSA event is likely to occur. In some embodiments of the present invention, any one or any combination of the above indications can be used to indicate the onset or the occurrence of an USA event. Such indications or any combination thereof can also be reviewed post an OSA occurrence such that the control circuit 130 is reprogrammed automatically post an OSA event to identify the sequence of indications leading to an OSA event that occurred with the specific patient.

FIG. 3 is a flow diagram 300 of the process of monitoring the position of position circuits 120, according to an exemplary embodiment of the invention. In an exemplary embodiment of the invention, reader 150 sends (310) a signal to position circuits 120. Optionally, if there is more than one position circuit 120 reader 150 may query the position circuits 120 sequentially or in parallel. In some embodiments of the invention, each position circuit 120 accepts a signal representing a different code and each position circuit 120 only responds to signals with its code. Alternatively, all the position circuits 120 accept the same code.

In an exemplary embodiment of the invention, the position circuits 120 respond (320) to the signal from reader 150. In some embodiments of the invention, each position circuit 120 responds with a different pre-selected delay time relative to the signal from reader 150, so that reader 150 will receive the responses one after another even if all the position circuits 120 receive the signal simultaneously.

In an exemplary embodiment of the invention, control 156 of reader 150 processes the responses from position circuits 120 and calculates (330) from the responses the relative location of each position circuit 120. Optionally, control 156 takes into account pre-selected delay times and if the position circuits are positioned with a non-varying distance or if their relative position is variable. In an exemplary embodiment of the invention, control 156 stores the details of the position in memory 158 and keeps track of the current position relative to the previous positions based on previous readings.

Optionally, control 156 can then determine (340) if an OSA event is about to take place, for example if the tongue muscle is collapsing so that it will block the airway. Optionally, control 156 can then determine (340) if an OSA event is about to take place based on the trajectory of the position circuits 120. Optionally, control 156 can then determine (340) if an OSA event is about to take place based on one or more indications as described here in above in conjunction with the description of FIG. 2, whether or not the indications were received in response to a signal sent to the position circuits 120.

Optionally, in step 340 the reader 150 can determine if an onset of an OSA event is likely, or if an OSA event has occurred in the past based on the various indications received. In an exemplary embodiment of the invention, as long as an OSA event is not about to occur, reader 150 will continue to query position circuits 120. In some embodiments of the invention, the querying is performed continuously. Alternatively, the querying may be performed periodically, for example 1000 times a second or 100 times a second. In some other embodiments of the invention, the reader will not query the position circuits, and the position circuits will continuously send indication or emit energy in response to which the reader 150 can determine the position of position circuits 120.

In some other embodiments of the present invention, the motion sensor 145 located in the implant 110 activates the position circuits 120 which in response emit energy or transmission upon in response to which the reader may determine the position of the position circuits 120.

In some embodiments of the invention, transceiver 152 transmits the signal from multiple positions along the length of reader 150. Optionally, the location of position circuits 120 are determined by comparing the timing of the responses or through an analysis of any one or more of the indications disclosed herein above.

In an exemplary embodiment of the invention, if reader 150 determines that an OSA event is about to take place (340) it may take (350) various remedial actions, for example notify an implanted stimulator (e.g. implant 110) to stimulate the muscle and prevent it from occurring. Alternatively or additionally, reader 150 may include a buzzer (not shown) that provides an audible or tactile alarm to alert the patient to the occurrence of an OSA event, for example in the diagnostic stage of treating the patient. Optionally, reader 150 records information regarding the occurrence of an OSA event in its memory 158, for example the time and date of the occurrence. In some embodiments of the invention, reader 150 may be connected either during usage or after usage to a computer to analyze data stored in memory 158. Optionally, reader 150 may record a sequence of indications leading to an OSA event in memory 158. Optionally, reader 150 may further in step 350 reprogram itself to identify a future OSA event or the onset of such an event based on previous sequences of events which led to an OSA event. Optionally, memory 158 may be a non-volatile memory so that the data is available even if power source 154 is depleted. In some embodiments of the invention, memory 158 is removable and can be read using a memory card reader, for example with a USB memory card reader.

In some embodiments of the invention, reader 150 is initially calibrated when it is first deployed, for example by requiring the patient to push his tongue forward and/or back during the first few minutes from activation, so that reader 150 can record the extreme possible locations occurring as a result of natural use of the tongue and use the data to compare with locations occurring later that result from muscle collapse during an OSA event.

In some embodiments of the invention, reader 150 is designed to be able to record a response from position circuits 120 in allowable or preapproved positions, when the tongue muscle is functioning. Optionally, if the tongue muscle collapses, position circuits 120 move out of range and reader 150 does not receive a response. In an exemplary embodiment of the invention, reader 150 determines if an OSA event is about to occur, based on the previous motion of position circuits 120, and optionally also from the fact that position circuits 120 stopped responding. Optionally, reader 150 may signal implant 110 to stimulate the tongue muscle, causing the tongue to return to its correct position and communications from position circuits 120 to resume.

In some embodiments of the invention, implant 110 may monitor the communications with position circuits 120 and if the communications cease since position circuits 120 are out of range, implant 110 will stimulate the tongue muscle without receiving an instruction from an external source. Alternatively, reader 150 may have separate communication systems for communicating with position circuits 120 and a separate communication system for communicating with implant 110. Optionally, the communication system for communicating with implant 110 has a greater range than the communication system for communicating with position circuits 120, so that if communications with position circuits 120 fail reader 150 can still provide instructions to implant 110 to take remedial actions.

FIG. 4 is a schematic block diagram of an alternative reader 450 and implant 410, according to an exemplary embodiment of the invention. Optionally, reader 450 includes a control 456, a memory 458 similar to the elements of reader 150. However in reader 450 in contrast to reader 150, position circuits 120 are embedded in reader 450 outside of the patient and not embedded in implant 410 that is embedded inside the tongue muscle of the patient. Optionally, reader 450 includes a power source 454 and a transceiver 452 that is adapted to wirelessly transmit power to tracking object 410. In an exemplary embodiment of the invention, implant 410 includes a control circuit 430, a transceiver 414 and a power receptor 412. Optionally, transceiver 452 transmits power wirelessly to power receptor 412. In an exemplary embodiment of the invention, when tracking object 410 begins to receive power from reader 450, transceiver 414 transmits signals to locate position circuits 120. Optionally, if the link is broken and tracking object 410 ceases to receive power from reader 450: it stops transmitting a signal for position circuits 120 and control circuit 430 may instruct implant 410 to stimulate the tongue muscle of the patient. In some embodiments of the invention, control circuit 430 will only stimulate the patient if there is a determination that the position of the tongue muscle is moving in a direction that will cause an OSA event. Optionally, if power source 454 of reader 450 is running low, for example below 10% left, it will notify tracking object 410 to shut off the stimulator.

In some embodiments of the invention, multiple readers 150 are used to monitor the location of position circuits 120, for example one reader may be positioned on the patient's cheek and the second reader under the patient's chin. Optionally the multiple readers 150 communicate with each other via transceiver 152, for example to compare the responses received from position circuits 120. In some cases one may receive a response from a specific position circuit 120 while the other does not due to the position of the tongue muscle. Optionally, implant 110 may be instructed to stimulate the tongue muscle only if there is a loss of a signal from more than one reader or only if all readers 150 don't provide a signal. Alternatively, implant 110 may be instructed to stimulate the tongue muscle if a single reader 150 doesn't provide a signal. Optionally, implant 110 may be instructed to stimulate the tongue muscle based on additional information, for example the trajectory of motion of the tongue.

In an exemplary embodiment of the invention, reader 150 may include additional sensors, for example:
 1. Sensors that provide surface EMG to detect movement of the tongue;
 2. Sensors that provide ultrasound imaging of the tongue and its location;
 3. Sensors that provide infrared imaging to sense temperature changes;
 4. Sensors that provide temperature measurements to detect changes in temperature due to decreased breathing;
 5. A contact microphone to detect vibrations due to snoring and obstruction of the air path;
 6. A contact microphone to record breathing sounds;
 7. Sensors that provide ECG measurements;
 8. Sensors that provide EEG measurements;
 9. Sensors that sense heart rate variability;
 10. Sensors that measure oxygen saturation;
 11. Sensors that measure movement;
 12. Sensors that measure motion; and
 13. Sensors that measure vector acceleration.

Optionally, reader 150 may incorporate any of the above measurements to enhance accuracy of the diagnosis and prediction of an OSA event.

FIG. 5 is a schematic block diagram of a tongue location monitoring system 500 with a reader 550 and a biodegradable tape 510 with position circuits 520 embedded therein, according to an exemplary embodiment of the invention.

Optionally, reader 550 is similar to reader 150 by including a control 556, a memory 558, a power source 554, an activation switch 559 and a transceiver 552. Optionally, biodegradable tape 510 is a biocompatible adhesive tape that is dissolvable, for example when in contact with the patient's saliva it dissolves within a few hours (e.g. between 1-8 hours: during the patient's sleep). Optionally, different tapes may be used with different lifetimes before being completely dissolved. In an exemplary embodiment of the invention, position circuits 520 (e.g. an RFID circuit) embedded therein are coated with a biocompatible enclosure 530 that is resistant to digestive fluids. Optionally, during the patient's sleep tape 510 dissolves and position circuits 520 are swallowed and later extracted through the digestive system. In an exemplary embodiment of the invention, a constant distance 540 is set between each position circuit 520. Alternatively, position circuits 120 may be positioned randomly on tape 510.

In an exemplary embodiment of the invention, biodegradable tape 510 is attached to a patient's tongue before going to sleep. Optionally, reader 550 is attached to the patient's head 105, or positioned or worn by the patient near his head 105, so that the transmissions from reader 550 will be received by position circuits 520 on tape 510. Optionally, reader 550 is activated and monitors the position of the patient's tongue during his/her sleep by transmitting signals to position circuits 520 as described above.

In an exemplary embodiment of the invention, the location data is stored in memory 558 to be taken out later and analyzed by a computer to diagnose obstructive sleep apnea. Alternatively or additionally, the data may be transmitted live by reader 558 to an external computer using a wireless connection (e.g. BT or WiFi or a cellular wan connection). In some embodiments of the invention, reader 558 is connected with a data cable to a computer (e.g. using a USB connection) to transmit the data while it is being collected. Optionally, the data is encrypted, compressed or manipulated by other methods (e.g. error correction schemes) to ensure its safe delivery to the correct target. Optionally, the data recorded by reader 558 may be used to determine if implantation of a stimulator is feasible for the patient. Additionally, the data recorded by reader 558 may be used to initially program an implantable stimulator based on the measurements, for example programming the intensity of stimulation based on the degree of collapse of the tongue for the specific patient.

In some embodiments of the invention, other measured data is combined to the data collected by reader 558, for example ECG or EEG data, to enhance the accuracy of the measurements.

In an exemplary embodiment of the invention, position circuits 520 may include surface EMG (electromyography) electrodes. Optionally, the electrodes sense EMG data from the tongue muscle and transmit the data to reader 558 with the other data from position circuits 520 (e.g. RFID tag ID information).

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the invention. Further combinations of the above features are also considered to be within the scope of some embodiments of the invention.

It will be appreciated by persons skilled in the art that the present invention is not limited to what has been particularly shown and described hereinabove. Rather the scope of the present invention is defined only by the claims, which follow.

We claim:

1. A tongue location monitoring system, comprising:
at least one position circuit configured to respond to wireless transmissions;
a transceiver configured to wirelessly transmit to the at least one position circuit;
a control circuit coupled to the transceiver;
wherein said control circuit determines the location of a person's tongue based on the responses of the at least one position circuit;
and wherein the at least one position circuit is configured for placement in or on the person's tongue, and the transceiver is configured for location outside the person's head.

2. A system according to claim 1, wherein said at least one position circuit is configured for implantation beneath the skin of the subject and on a muscle of the tongue.

3. A system according to claim 1, wherein said at least one position circuit is embedded in an implantable stimulator that is configured to be implanted in the tongue muscle and said implantable stimulator is adapted to stimulate the tongue muscle.

4. A system according to claim 1, wherein said at least one position circuit is embedded in a biodegradable tape that is configured to be adhesively attached to the tongue.

5. A system according to claim 1, wherein said control circuit determines the location of the tongue based on the travel time of the signal to the at least one position circuit and back.

6. A system according to claim 1, wherein said control circuit determines the location of the tongue based on the strength of the signal returning to the transceiver.

7. A system according to claim 1, wherein an obstructive sleep apnea event is detected by monitoring the location of the tongue.

8. A system according to claim 1, wherein an obstructive sleep apnea event is detected by monitoring the angle of arrival of a response signal from the at least one position circuit.

9. A system according to claim 1, wherein the at least one position circuit is a plurality of position circuits, and the plurality of position circuits are queried sequentially.

10. A system according to claim 1, wherein the at least one position circuit is a plurality of position circuits, and the plurality of position circuits are queried in parallel.

11. A system according to claim 1, wherein the at least one position circuit is queried continuously.

12. A system according to claim 1, wherein the at least one position circuit is queried periodically.

13. A system according to claim 1, wherein the transceiver is provided power wirelessly and the transceiver queries the at least one position circuit as long as it is provided power wirelessly.

14. A method of monitoring the location of the tongue, comprising:
positioning a transceiver outside a head of a person;
transmitting signals from the transceiver to at least one position circuit positioned in or on a tongue of the person;
receiving a response from the at least one position circuit;
calculating the location of the at least one position circuit relative to the transceiver from the response;
determining if an obstructive sleep apnea event is about to occur based on the calculated locations.

15. A method according to claim 14, wherein the at least one position circuit is implanted beneath the skin of the subject and on a muscle of the tongue.

16. A method according to claim 14, further comprising stimulating the muscle of the tongue in response to the determining of an obstructive sleep apnea event.

* * * * *